(12) United States Patent
Mattner

(10) Patent No.: US 7,732,568 B2
(45) Date of Patent: Jun. 8, 2010

(54) METHODS FOR PREVENTING AND TREATING ALZHEIMER'S DISEASE

(75) Inventor: Frank Mattner, Vienna (AT)

(73) Assignee: AFFIRIS Forschungs-und Entwicklungs GmbH, Vienna (AT)

( * ) Notice: Subject to any disclaimer, the term of this patent is extended or adjusted under 35 U.S.C. 154(b) by 886 days.

(21) Appl. No.: 10/540,551

(22) PCT Filed: Jan. 13, 2004

(86) PCT No.: PCT/EP2004/000162

§ 371 (c)(1),
(2), (4) Date: Oct. 11, 2005

(87) PCT Pub. No.: WO2004/062556

PCT Pub. Date: Jul. 29, 2004

(65) Prior Publication Data

US 2006/0111301 A1    May 25, 2006

(30) Foreign Application Priority Data

Jan. 14, 2003  (AT)  ................. A 36/2003
Sep. 17, 2003  (AT)  ................. A1464/2003

(51) Int. Cl.
*A61K 38/00*  (2006.01)

(52) U.S. Cl. .................................. 530/326

(58) Field of Classification Search .................. None
See application file for complete search history.

(56) References Cited

U.S. PATENT DOCUMENTS 6,083,722 A * 7/2000 Bergstrom et al. ......... 435/69.3
6,703,491 B1 * 3/2004 Homburger et al. ........ 536/23.1

FOREIGN PATENT DOCUMENTS

| EP | 1 361 439 | 11/2003 |
|----|-----------|---------|
| WO | 92/07077 | 4/1992 |
| WO | 00/50077 | 8/2000 |
| WO | 00/72880 | 12/2000 |
| WO | WO 00/72880 | * 12/2000 |
| WO | 01/64008 | 9/2001 |
| WO | 02/2888 | 4/2002 |

OTHER PUBLICATIONS

Abadie et al, "Specific and total IgE responses to antigenic stimuli in Brown-Norway, Lewis and Sprague-Dawley rats," Immunology (1980), vol. 39 561-569.*

Eichler J et al, Identification of Substrate-Analog Trypsin Inhibitors through the Screening of Synthetic Peptide Combinatorial Libraries, Biochemistry 1993, 32, 11035-11041.*

Reineke U et al: "Identification of distinct antibody epitopes and mimotopes from a peptide array of 5520 randomly generated sequences" Journal of Immunological Methods, vol. 267, No. 1, Sep. 1, 2002, pp. 37-51, XP004372978 ISSN: 0022-1759 cited in the application, the whole document.

McLaurin J et al: "Therapeutically effective antibodies against amyloid-beta peptide target amyloid-beta residues 4-10 fibrillogenesis." Nature Medicine, vol. 8, No. 11, Nov. 2002, pp. 1263-1269, XP002288573, ISSN: 1078-8956, abstract, p. 1266, right-hand column, last paragraph—p. 1267, right-hand column, last paragraph.

* cited by examiner

*Primary Examiner*—Cecilia Tsang
*Assistant Examiner*—Thomas S Heard
(74) *Attorney, Agent, or Firm*—Oblon, Spivak, McClelland, Maier & Neustadt, L.L.P.

(57) ABSTRACT

The present invention relates to methods for preventing and treating Alzheimer's disease (AD). An Aβ42 mimotope is used for vaccination against AD. The mimotope induces the production of antibodies against Aβ42 but not against the native APP. The mimotope is functionally similar to, but not structurally identical with DAEFRH (SEQ ID NO: 1) which is a part of the naturally-occurring Aβ42 sequence.

34 Claims, 5 Drawing Sheets

Fig.1A

| 1 | alanine | ala | A |
| 2 | arginine | arg | R |
| 3 | asparagine | asn | N |
| 4 | aspartic acid | asp | D |
| 5 | cysteine | cys | C |
| 6 | glutamine | gln | Q |
| 7 | glutamic acid | glu | E |
| 8 | glycine | gly | G |
| 9 | histidine | his | H |
| 10 | isoleucine | ile | I |
| 11 | leucine | leu | L |
| 12 | lysine | lys | K |
| 13 | methionine | met | M |
| 14 | phenylalanine | phe | F |
| 15 | proline | pro | P |
| 16 | serine | ser | S |
| 17 | threonine | thr | T |
| 18 | tryptophan | trp | W |
| 19 | tyrosine | tyr | Y |
| 20 | valine | val | V |

Fig.1B

| No. | D | A | E | F | R | H | |
|---|---|---|---|---|---|---|---|
| 1 | D | A | E | F | R | H | positive control |
| 2 | D | R | E | F | R | H | |
| 3 | D | N | E | F | R | H | |
| 4 | D | D | E | F | R | H | |
| 5 | D | Q | E | F | R | H | |
| 6 | D | E | E | F | R | H | |
| 7 | D | G | E | F | R | H | |
| 8 | D | H | E | F | R | H | |
| 9 | D | I | E | F | R | H | |
| 10 | D | L | E | F | R | H | |
| 11 | D | M | E | F | R | H | |
| 12 | D | F | E | F | R | H | |
| 13 | D | P | E | F | R | H | |
| 14 | D | S | E | F | R | H | |
| 15 | D | T | E | F | R | H | |
| 16 | D | W | E | F | R | H | |
| 17 | D | Y | E | F | R | H | |
| 18 | D | V | E | F | R | H | |
| 19 | D | A | A | F | R | H | |
| 20 | D | A | R | F | R | H | |
| 21 | D | A | N | F | R | H | |
| 22 | D | A | D | F | R | H | |
| 23 | D | A | Q | F | R | H | |
| 24 | D | A | E | F | R | H | positive control |
| 25 | D | A | G | F | R | H | |
| 26 | D | A | H | F | R | H | |
| 27 | D | A | I | F | R | H | |
| 28 | D | A | L | F | R | H | |
| 29 | D | A | M | F | R | H | |
| 30 | D | A | F | F | R | H | |
| 31 | D | A | P | F | R | H | |
| 32 | D | A | S | F | R | H | |
| 33 | D | A | T | F | R | H | |
| 34 | D | A | W | F | R | H | |
| 35 | D | A | Y | F | R | H | |
| 36 | D | A | V | F | R | H | |
| 37 | D | A | E | A | R | H | |
| 38 | D | A | E | R | R | H | |
| 39 | D | A | E | N | R | H | |
| 40 | D | A | E | D | R | H | |
| 41 | D | A | E | Q | R | H | |
| 42 | D | A | E | E | R | H | |
| 43 | D | A | E | G | R | H | |
| 44 | D | A | E | H | R | H | |
| 45 | D | A | E | I | R | H | |
| 46 | D | A | E | L | R | H | |
| 47 | D | A | E | M | R | H | |
| 48 | D | A | E | F | R | H | positive control |
| 49 | D | A | E | P | R | H | |
| 50 | D | A | E | S | R | H | |

Fig.1C

| | | | | | | |
|---|---|---|---|---|---|---|
| 51 | D | A | E | T | R | H |
| 52 | D | A | E | W | R | H |
| 53 | D | A | E | Y | R | H |
| 54 | D | A | E | V | R | H |
| 55 | D | A | E | F | A | H |
| 56 | D | A | E | F | R | H | positive control
| 57 | D | A | E | F | N | H |
| 58 | D | A | E | F | D | H |
| 59 | D | A | E | F | Q | H |
| 60 | D | A | E | F | E | H |
| 61 | D | A | E | F | G | H |
| 62 | D | A | E | F | H | H |
| 63 | D | A | E | F | I | H |
| 64 | D | A | E | F | L | H |
| 65 | D | A | E | F | M | H |
| 66 | D | A | E | F | F | H |
| 67 | D | A | E | F | P | H |
| 68 | D | A | E | F | S | H |
| 69 | D | A | E | F | T | H |
| 70 | D | A | E | F | W | H |
| 71 | D | A | E | F | Y | H |
| 72 | D | A | E | F | V | H |
| 73 | D | A | E | F | R | A |
| 74 | D | A | E | F | R | R |
| 75 | D | A | E | F | R | N |
| 76 | D | A | E | F | R | D |
| 77 | D | A | E | F | R | Q |
| 78 | D | A | E | F | R | E |
| 79 | D | A | E | F | R | G |
| 80 | D | A | E | F | R | H | positive control
| 81 | D | A | E | F | R | I |
| 82 | D | A | E | F | R | L |
| 83 | D | A | E | F | R | M |
| 84 | D | A | E | F | R | F |
| 85 | D | A | E | F | R | P |
| 86 | D | A | E | F | R | S |
| 87 | D | A | E | F | R | T |
| 88 | D | A | E | F | R | W |
| 89 | D | A | E | F | R | Y |
| 90 | D | A | E | F | R | V |

METHODS FOR PREVENTING AND TREATING ALZHEIMER'S DISEASE

BACKGROUND OF THE INVENTION

1. Field of the Invention

The present invention relates to methods for preventing and treating Alzheimer's disease (AD).

2. Description of Related Art

Amyloid-β peptide (Aβ) plays a central role in the neuropathology of Alzheimer's disease (AD) (Roher et al 1993: "β-Amyloid-(1-42) is a major component of cerebrovascular amyloid deposits: Implications for the pathology of Alzheimer disease" PNAS 90:10836). Familial forms of the disease have been linked to mutations in the amyloid precursor protein (APP) and the presenilin genes. Disease-linked mutations in these genes result in increased production of the 42-amino acid form of the peptide (Aβ42), which is the predominant form found in the amyloid plaques of Alzheimer's disease. An animal model for the disease is commercially available. The PDAPP transgenic mouse, which overexpresses mutant human APP (in which the amino acid at position 717 is F instead of V), progressively develops many of the neuropathological hallmarks of Alzheimer's disease in an age- and brain-dependent manner (Games et al 1995: "Alzheimer-type neuropathology in transgenic mice overexpressing V717β-amyloid precursor protein" Nature 373:523).

Vaccination studies with a "normal", not mimotope-based vaccine have already been performed. Transgenic animals were immunized with aggregated Aβ42, either before the onset of AD-type neuro-pathologies (6 weeks) or at an older age (11 months): Immunization of young animals prevented the development of plaque formation, neuritic dystrophy and astrogliosis. Treatment of older animals markedly reduced AD-like neuropathologies. This experimental vaccination approach induced the development of antibodies against Aβ42 able to cross the blood-brain barrier and attack amyloid plaques (Schenk et al 1999: "Immunization with amyloid-β attenuates Alzheimer-disease-like pathology in the PD-APP mouse" Nature 400:173). The plaques are subsequently removed by several mechanisms, including Fc-receptor mediated phagocytosis (Bard et al 2000: "Peripherally administered antibodies against amyloid β-peptide enter the central nervous system and reduce pathology in a mouse model of Alzheimer disease" Nature Med 6:916). This vaccine was also able to delay memory deficits (Janus et al 2000: "Aβ peptide immunization reduces behavioural impairment and plaques in a model of Alzheimer's disease" Nature 408:979).

A highly promising immunization therapy for AD has been in clinical trials since late 1999. Immunization is presumed to trigger the immune system to attack the plaques and clear these deposits from the affected human brain, although the precise mechanism underlying needs to be characterized in more detail.

These clinical trials were conducted by the pharmaceutical company Elan in conjunction with its corporate partner, American Home Products (therapeutic vaccine AN-1792, QS21 as adjuvant). Phase I trials were successfully completed in 2000. Phase II trials were begun late 2001 to test efficacy in a panel of patients with mild to moderate AD.

Now these phase II trials have been permanently discontinued due to neuroinflammation in several patients (Editorial 2002 "Insoluble problem?" Nature Med 8:191). The symptoms included aseptic meningoencephalitis leading to the immediate halt of these world-wide trials. In the worst case scenario, affected patients will be shown to have mounted an autoimmune response—a risk inherent in many immunotherapies. Autoimmune complications could have been anticipated given the ubiquity of APP, which of course bears antigenic determinants in common with its proteolytic product. More recently, additional studies concentrated on the nature of aggregated Aβ42 immunization-induced antibodies (in humans and mice) revealing that most antibodies recognize a small domain between amino acid 4 and 10 of Aβ42 (Aβ4-10). The mouse antibodies were able to block Afl fibrillogenesis and disrupted pre-existing Aβ fibers (McLaurin et al 2002: "Therapeutically effective antibodies against amyloid-β peptide target amyloid-β residues 4-10 and inhibit cytotoxicity and fibrillogenesis" Nature Med 8:1263). Of note, the human antibodies do not react with APP exposed on the surface of cells or any other non-aggregated proteolytic product of the precursor (Hock et al 2002: "Generation of antibodies specific for β-amyloid by vaccination of patients with Alzheimer disease" Nature Med 8:1270).

A clear difference was observed between human and mouse sera: In contrast to human antibodies, mouse antibodies detect monomeric, oligomeric, and fibrillar Aβ. This is of importance and may be a prerequisite for the therapeutic potency since evidence is accumulating that small oligomers of Aβ, which are not recognized by human anti-AO, are the major toxic players in the disease (Walsh et al 2002: "Naturally secreted oligomers of amyloid β protein potently inhibit hippocampal long-term potentiation in vivo" Nature 416:535). Thus, a potential new strategy is the immunization with a vaccine containing β-amyloid amino acids 4-10 (instead of aggregated Aβ42). Despite unknown efficacy this strategy may also face autoimmune problems since patients shall be directly immunized with a (linear B cell) "self" epitope.

Despite these disappointing developments in recent AD vaccination strategies, an Aβ vaccine is still regarded as the most promising way for combatting AD. However, there is an urgent need for improvements and new strategies in AD vaccination. Especially, such a vaccine should not induce autoreactive T and/or B. cells.

BRIEF DESCRIPTION OF THE INVENTION

Therefore, the present invention provides the use of a compound comprising the following amino acid sequence

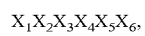

wherein $X_1$ is an amino acid, except of C, $X_2$ is an amino acid, except of C, $X_3$ is an amino acid, except of C, $X_4$ is an amino acid, except of C, $X_5$ is an amino acid, except of C, $X_6$ is an amino acid, except of C, and wherein $X_1X_2X_3X_4X_5X_6$ is not DAEFRH (SEQ ID NO: 1), said compound having a binding capacity to an antibody being specific for the natural N-terminal Aβ42 sequence DAEFRH (SEQ ID NO: 1), and 5-mers thereof having a binding capacity to said antibody being specific for the natural N-terminal Aβ42 sequence DAEFRH (SEQ ID NO: 1), for the preparation of a vaccine for Alzheimer's disease (AD).

BRIEF DESCRIPTION OF THE DRAWINGS

FIG. 1 shows the individualized peptide members of library 4 used for the present screening process (SEQ ID NOS: 1-90).

DETAILED DESCRIPTION OF THE PREFERRED EMBODIMENTS

Figure 2:
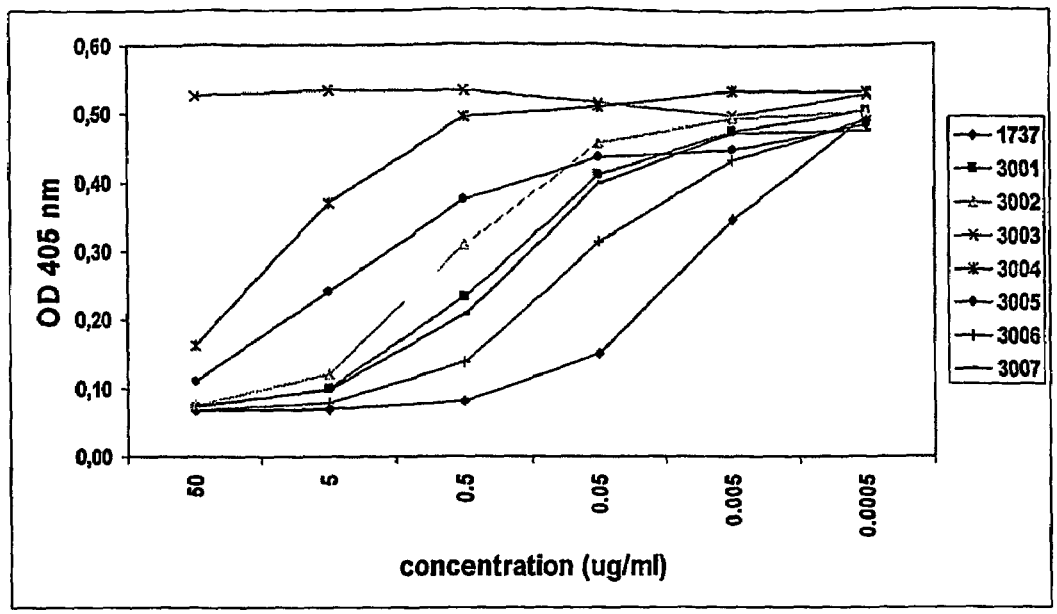
FIG. 2 shows an inhibition assay with mimotopes for DAE-FRH (SEC) ID NO: 1).

According to the present invention an Aβ42 mimotope is used for vaccination against AD: The mimotope induces the production of antibodies against Aβ42 but not against the native APP. The mimotope may be identified with a (monoclonal) antibody and (commercially available) peptide libraries (e.g. according to Reineke et al. 2002: "Identification of distinct antibody epitopes and mimotopes from a peptide array of 5520 randomly generated sequences" J Immunol methods 267:37). A (monoclonal) antibody is used that does not recognize APP but detects only different Aβ3 species with amino-terminal aspartic acid (an example for such an antibody is described in Johnson-Wood et al 1997: "Amyloid precursor protein processing and Aβ42 deposition in a transgenic mouse model of Alzheimer disease" PNAS 94:1550). Such an antibody has been proven to be an ideal tool to identify vaccine-suitable mimotopes in the course of the present invention. Although such monoclonal antibodies were shown to have beneficial effects in a mouse model of AD when directly administered to mice (Bard et al 2000: "Peripherally administered antibodies against amyloid β-peptide enter the central nervous system and reduce pathology in a mouse model of Alzheimer disease" Nature Med 6:916), these antibodies have never been proposed to be used as mimotope search tools for isolating AD vaccine compounds.

In the prior art, all efforts were concentrated on the naturally occurring Aβ peptide. As mentioned above, V peptide vaccine clinical trials were stopped due to neuroinflammation events. Indeed, T cell epitope prediction programs (BIMAS for class I-restricted epitopes and TEPITOPE for class II-restricted epitopes) propose high score (self) epitopes within the sequence. This could imply that the neuroinflammatory events are due to autoimmune reactions which would make such a vaccine unsuitable for a general application.

In contrast to such Aβ vaccines proposed by the prior art, no autoimmune reactions are expected to occur during treatment with a vaccine containing a mimotope according to the present invention, because the (monoclonal) antibody used for mimotope identification according to the present invention does not recognize APP and the mimotope sequence is different from Aβ42-derived self sequences that have been used in trials so far or shall be used in future trials.

The antibody used for the mimotope identification according to the present invention detects the Aβ-derived amino acid sequence DAEFRH (SEQ ID NO: 1) (=original epitope) with a free amino terminal aspartic acid, thus it does not recognize native APP. The antibody may be a monoclonal or polyclonal antibody preparation or any antibody part or derivative thereof, the only prerequisite is that the antibody molecule specifically recognises the DAEFRH (SEQ ID NO: 1) epitope, i.e. that it does not bind to the natural N-terminally prolonged forms of the amyloid precursor protein, which means that the binding capacity to the DAEFRH (SEQ ID NO: 1) epitope is at least 100 times, preferably at least 1000 times, more preferred at least $10^5$ times, higher than to the APP molecule. The antibody may be an antibody showing the same or a higher binding capacity to the DAEFRH (SEQ ID NO: 1) sequence as the antibody described by Johnson-Wood et al., 1997. Of course, also antibodies with a lower binding capacity may be used (>10%, >50% or >80% of the binding capacity of the Johnson-Wood et al. antibody), although the higher binding capacity is more preferred.

The compounds according to the present invention bind to those antibodies with comparable specificity as the DAEFRH (SEQ ID NO: 1) sequence.

Preferably, the compound to be used according to the present invention comprises or is consisting of a peptide, wherein $X_1$ is G or an amino acid with a hydroxy group or a negatively charged amino acid, preferably E, Y, S or D, $X_2$ is a hydrophobic amino acid or a positively charged amino acid, preferably I, L, V, K, W, R, Y, F or A, $X_3$ is a negatively charged amino acid, preferably D or E, $X_4$ is an aromatic amino acid or L, preferably Y, F or L, $X_5$ is H, K, Y, F or R, preferably H, F or R, and $X_6$ is S, T, N, Q, D, E, R, I, K, Y, or G, preferably T, N, D, R, I or G, especially EIDYHR (SEQ ID NO: 91), ELDYHR (SEQ ID NO: 92), EVDYHR (SEQ ID NO: 93), DIDYHR (SEQ ID NO: 94), DLDYHR (SEQ ID NO: 95), DVDYHR (SEQ ID NO: 96), DIDYRR (SEQ ID NO: 97), DLDYRR (SEQ ID NO: 98), DVDYRR (SEQ ID NO: 99), DKELRI (SEQ ID NO: 100), DWELRI (SEQ ID NO: 101), YREFRI (SEQ ID NO: 102), YAEFRG (SEQ ID NO: 103), EAEFRG (SEQ ID NO: 104), DYEFRG (SEQ ID NO: 105), ELEFRG (SEQ ID NO: 106), DRELRI (SEQ ID NO: 107), DKELKI (SEQ ID NO: 108), DRELKI (SEQ ID NO: 109), GREFRN (SEQ ID NO: 110), EYEFRG (SEQ ID NO: 111), DWEFRDA (SEQ ID NO: 112), SWEFRT (SEQ ID NO: 113), DKELR (SEQ ID NO: 114) or SFEFRG (SEQ ID NO: 115).

The compound (mimotope) according to the present invention has a preferred length of 5 to 15 amino acids. This compound may be provided in the vaccine in isolated (peptide) form or may be coupled or complexed to other molecules, such as pharmaceutical carrier substances or polypeptide, lipid or carbohydrate structures. Preferably, the mimotopes according to the present invention have a (minimum) length of between 5 and 15, 6 and 12 amino acid residues, specifically between 9 and 11. The mimotopes can, however, be coupled (covalently or non-covalent) to unspecific linkers or carriers, especially peptide linkers or protein carriers. Furthermore, the peptide linkers or protein carriers might consist of or contain T-cell helper epitopes.

Preferably, the pharmaceutically acceptable carrier is KLH, tetanus toxoid, albumin binding protein, bovine serum albumin, a dendrimer (MAP; *Biol. Chem.* 358:581) as well as the adjuvant substances described in Singh et al., Nat. Biotech. 17 (1999), 1075-1081 (specifically those in table 1 of this document) and O'Hagan et al., Nature Reviews, Drug Discovery 2(9)(2003), 727-735 (specifically the innate immune-potentiating compounds and the delivery systems described therein), or mixtures thereof. In addition, the vaccine composition may contain aluminium hydroxyde.

A vaccine comprising the present compound (mimotope) and the pharmaceutically acceptable carrier may be administered by any suitable application mode, e.g. i.v., i.p., i.m., intranasal, oral, subcutaneous, etc. and in any suitable delivery device (O'Hagan et al., Nature Reviews, Drug Discovery 2(9)(2003), 727-735). Typically, the vaccine contains the compound according to the present invention in an amount of 0.1 ng to 10 mg, preferably 10 ng to 1 mg, especially 100 ng to 100 μg or, alternatively e.g. 100 fmole to 10 μmole, preferably 10 pmole to 1 μmole, especially 100 pmole to 100 nmole. The vaccine may also comprise typical auxiliary substances, e.g. buffers, stabilizers, etc.

According to another aspect, the present invention further relates to a method for isolating a compound binding to an anti-body being specific for the natural N-terminal Aβ42 sequence DAEFRH (SEQ ID NO: 1) comprising the steps of
providing a peptide compound library comprising peptides containing the following amino acid sequence
$X_1X_2X_3X_4X_5X_6$ (SEQ ID NO: 91),
wherein $X_1$ is an amino acid, except of C,
$X_2$ is an amino acid, except of C,
$X_3$ is an amino acid, except of C,
$X_4$ is an amino acid, except of C,
$X_5$ is an amino acid, except of C,
$X_6$ is an amino acid, except of C,
and wherein $X_3X_4X_5X_6$ is not DAEFRH (SEQ ID NO: 1),
contacting said peptide library with said antibody and
isolating those members of the peptide library which bind to said antibody.

According to another aspect, the present invention further relates to a method for isolating a compound binding to an antibody being specific for the natural N-terminal Aβ42 sequence DAEFRH (SEQ ID NO: 1) comprising the steps of
providing a peptide compound library comprising peptides containing the following amino acid sequence $X_1X_2X_3X_4X_5X_6$, wherein $X_1$ is an amino acid, except of C, $X_2$ is an amino acid, except of C, $X_3$ is an amino acid, except of C, $X_4$ is an amino acid, except of C, $X_5$ is an amino acid, except of C, $X_6$ is an amino acid, except of C, and wherein $X_1X_2X_3X_4X_5X_6$ is not DAEFRH (SEQ ID NO: 1),
contacting said peptide library with said antibody and
isolating those members of the peptide library which bind to said antibody.

According to a specific embodiment of this aspect, the present invention relates to a method for isolating a compound binding to an antibody being specific for the natural N-terminal Aβ42 sequence DAEFRH (SEQ ID NO: 1) comprising the steps of
providing a peptide compound library comprising peptides containing the following amino acid sequence $X_1X_2X_3X_4X_5X_6$, wherein $X_1$ is a natural amino acid, except of K and C, $X_2$ is a natural amino acid, except of C, $X_3$ is a natural amino acid, except of K and C, $X_4$ is a natural amino acid, except of K and C, $X_5$ is a natural amino acid, except of C, $X_6$ is a natural amino acid, except of P and C, and wherein $X_1X_2X_3X_4X_5X_6$ is not DAEFRH (SEQ ID NO: 1),
contacting said peptide library with said antibody and
isolating those members of the peptide library which bind to said antibody.

Isolating suitable 5-mers according to the present invention can be achieved in the way described above, adapted to libraries with 5 amino acid variables, and may preferably be performed either by screening a library having amino acid variables $X_1$ to $X_5$ as described herein or by identifying suitable 5-mers in a positive member screened in a 6-mer-library (see: above). In the same way, also 7-mer, 8-mer, 9-mer, 10-mer, . . . libraries may be applied accordingly to screen for suitable sequences which bind to the present antibody-type. Suitable antibody-binding fragments of such longer sequences can be found, e.g. by testing these fragments with a length of 5, 6, 7, 8, 9, . . . amino acid residues for binding to the present antibody.

Such a method has been proven to be successful for providing Aβ mimotopes according to the present invention.

Preferably, said peptides are provided in individualised form in said library, especially immobilised on a solid surface, such as e.g. possible with the MULTIPIN™ peptide technology. The library may also be provided as a peptide mixture and the antibody:peptide complexes may be isolated after antibody binding. Alternatively, the antibody may be immobilised and the peptide library (in suspension or solution) is then contacted with the immobilised antibodies.

Preferably, the screening antibodies (or the members of the peptide library) comprise a suitable marker which allows the detection or isolation of the antibody or the antibody:peptide complex when bound to a peptide of the library. Suitable marker systems (i.a. biotinylation, fluorescence, radioactivity, magnetic markers, colour developing markers, secondary antibodies) are readily available to the skilled man in the art.

The library has to be constructed to exclude the naturally occurring Aβ sequence (e.g. DAEFRH (SEQ ID NO: 1)), since vaccination with this sequence is clearly excluded from this invention.

A further suitable technique for isolating the epitopes according to the present invention is screening in phage-peptide libraries as e.g. described in WO 03/020750.

The present invention also relates to a composition comprising an anti N-terminal Aβ42-antibody-binding peptide (or, in certain cases preferred, a larger molecule comprising such a peptide (e.g. the peptide linked to a carrier or delivery molecule)) as defined herein (optionally as single effective component), preferably to a vaccine against Alzheimer's Disease comprising such an antigen, especially an antigen which includes at least one peptide selected from the group EIDYHR (SEQ ID NO: 91), ELDYHR (SEQ ID NO: 92), EVDYHR (SEQ ID NO: 93), DIDYHR (SEQ ID NO: 94), DLDYHR (SEQ ID NO: 95), DIDYHR (SEQ ID NO: 96), DIDYRR (SEQ ID NO: 97), DLDYHR (SEQ ID NO: 98), DVDYRR (SEQ ID NO: 99), DKELRI (SEQ ID NO: 100), DWELRI (SEQ ID NO: 101), YREFRI (SEQ ID NO: 102), YAEFRG (SEQ ID NO: 103), EAEFRG (SEQ ID NO: 104), DYEFRG (SEQ ID NO: 105), ELEFRG (SEQ ID NO: 106), DRELRI (SEQ ID NO: 107), DKELKI (SEQ ID NO: 108), DRELKI (SEQ ID NO: 109), GREFRN (SEQ ID NO: 110), EYEFRG (SEQ ID NO: 111), DWEFRDA (SEQ ID NO: 112), SWEFRT (SEQ ID NO: 113), DKELR (SEQ ID NO: 114) or SFEFRG (SEQ ID NO: 115). These peptides are—besides the other peptides provided with the present invention specifically suited to be used for the preparation of a pharmaceutical composition, especially for AD vaccines. These sequences are purely artificial Aβ-mimotopes. The peptides may—for vaccination purposes—be coupled (covalently or non-covalently) to suitable carriers and may be provided as peptide compounds or complexes together with other compounds or moieties, e.g. adjuvants, peptide or protein carriers, etc. and administered in a suitable manner (as e.g. described in O'Hagan et al., Nature Reviews, Drug Discovery 2(9)(2003), 727-735).

The invention is further described in the following examples and the drawing figures, of course without being restricted thereto.

FIG. 1 shows the individualised peptide members of library 4 used for the present screening process (SEQ ID NOS 1 and 1-90, respectively, in order of appearance).

FIG. 2 shows an inhibition assay with mimotopes for DAEFRH (SEQ ID NO: 1).

Figure 3:
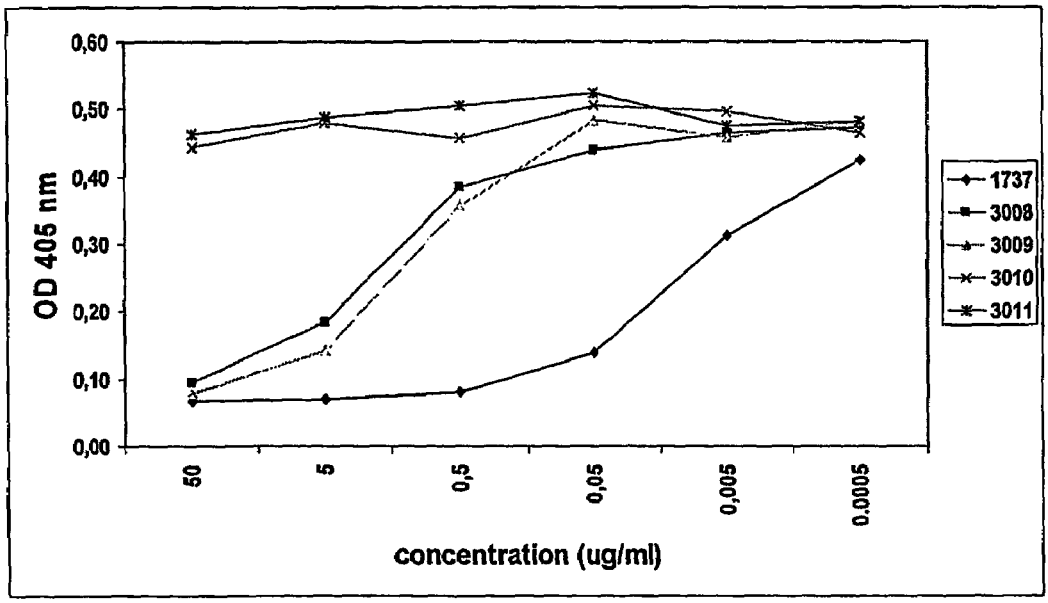
FIG. 3 shows another inhibition assay with other mimotopes for DAEFRH (SEQ ID NO: 1).

FIG. 3 shows another inhibition assay with other mimotopes for DAEFRH (SEQ ID NO: 1).

EXAMPLES

1.: Generation of Monoclonal Antibodies (mAb) to Detect Aβ42-Derived Peptide Species with Free N-Terminus (Free Aspartic Acid at the N-Terminus)

Mice are vaccinated with the 6mer peptide DAEFRH (SEQ ID NO: 1) (natural N-terminal Aβ42 sequence) linked to the protein bovine serum albumin BSA (to make use of the hapten-carrier-effect), emulsified in CFA (first injection) and IFA (booster injections). DAEFRH-peptide-specific (DAEFRH sequence disclosed as SEQ ID NO: 1), antibody-producing hybridomas are detected by ELISA (DAEFRH-peptide-coated ELISA plates (DAEFRH sequence disclosed as SEQ ID NO: 1)). Peptide SEVKMDAEFRH (SEQ ID NO: 116) (natural N-terminally prolonged sequence, APP-derived, containing the Aβ42-derived sequence DAEFRH (SEQ ID NO: 1)) is used as negative control peptide: hybridomas recognizing the prolonged peptide are excluded because they do not distinguish between Aβ42-derived peptides with free aspartic acid at the N-terminus and APP-derived peptide DAEFRH (SEQ ID NO: 1) without free aspartic acid.

2.: Construction of Peptide Libraries

The mimotopes of the present invention have been found by adapting the method of Reinke et al., 2000, by screening peptide libraries for binding to an antibody (preferably a monoclonal anti-body) which is specific for Aβ species with amino-terminal aspartic acid. Another method is commercially available as MULTIPIN™ peptide technology.

The Multipin™ peptide technology involves synthesizing peptides on to specially prepared polyethylene pins mounted on blocks in a format which is compatible with the standard 8×12 microtiter plate used for many biological assays. Both pin-bound (non-cleavable peptides which remain covalently bound to the pin) and solution phase peptides (those that have been cleaved off the pin surface) can be produced by this method. PepSets, based on the Multipin synthesis system, permit the simultaneous synthesis and screening of large numbers of peptides.

PepSets consist of blocks of 96 individually synthesized peptides, two of which are carefully selected control sequences. Cleaved controls are assessed for purity by reverse phase HPLC and peptide content quantitated by amino acid analysis. Positive and negative non-cleavable controls are assessed by standard ELISA techniques.

PepSet peptides are available with a variety of chemical modifications including acetylation, biotinylation, phosphorylation and cyclization. The solution phase (cleaved) peptides are shipped as lyophilized powders.

For the production of solution phase peptides there is a choice of C-terminal endings, including acid and amide, depending on the intended peptide application. The cleavable bond is incorporated onto the pin surface, either as a pre-formed ester derivative of the C-terminal amino acid, or onto the "Rink" amide linker. Peptides with acid or amide end groups are then released by treating the pin-bound peptide with strong acid. Options for the scale of synthesis are a nominal 1 micromole or 5 micromole scale. Factors such as hydrophobicity and cleavage efficiency will affect peptide recovery, such that the expected yield of peptide is 0.5 to 1 micromole (around 1 mg of a 15mer peptide) when the peptides are synthesized on the nominal 1 micromole scale, or a yield of 2.5 to 5 micromole for peptides synthesized on the nominal 5 micromole scale.

Non-cleavable peptides remain covalently bound to the pins and can be used to rapidly screen for peptides of interest using ELISA techniques. Such peptides are useful for the purposes of antibody epitope scanning and structure-activity relationship (SAR) studies. Removal of bound antibodies or other proteins regenerates the peptides and allows their reuse in further assays. PepSets are used for a variety of applications including the identification of peptide leads of biological interest from scanning through protein sequences, the optimization of peptide leads, and the development of new generations of analogs. Flexibility in terms of the overall strategy used in screening procedures is greatly enhanced through the use of a variety of synthesis designs which together provide a systematic method to fully characterize the lead candidate.

The comprehensive results obtained from systematic peptide sets not only identify peptides of interest, but also indicates critical residues, their replaceability and optimal peptide length. Consequently, a range of related peptides may be ranked as a result of such findings. Replacement of L-amino acids with D-amino acids and other unusual residues is a powerful approach to manipulate the structure and conformation of a peptide. This method is also a rapid way to discover new analogs with different pharmacological properties, such as antagonists and peptides with increased stability.

Starting with a known protein sequence, all sequential antibody epitopes can be mapped using the Multipin approach. Several alternative procedures for mapping sequential B-cell epitopes are now possible. These include pin-bound peptides, solution phase peptides coated directly onto microtiter plates, and biotinylated peptides captured on microtiter plates previously coated with avidin or streptavidin.

For the present examples, the antibody described in example 1 is used for screening peptide libraries, however, any antibody preparation specifically recognizing the DAEFRH-sequence (SEQ ID NO: 1), but not the naturally N-terminally prolonged sequence of the Aβ molecule (e.g. MDAEFRH (SEQ ID NO: 117), KMDAEFRH (SEQ ID NO: 118), SEVKMDAEFRH (SEQ ID NO: 116) or the complete amyloid (precursor) protein, APP), such as e.g. described by Johnson-Wood et al., 1997.

Four libraries have been constructed for this purpose:

2.1.: Library 1: This 6mer library contains peptides with the following sequences (amino acid positions 1 to 6):

Position 1: all natural as except of D, K, and C (17 possibilities)

Position 2: all natural as except of A, K, and C (17 possibilities)

Position 3: all natural as except of E, K, and C (17 possibilities)

Position 4: all natural as except of F, K, and C (17 possibilities)

Position 5: all natural as except of R, K, and C (17 possibilities)

Position 6: all natural as except of H, K, C, and P (16 possibilities)

Library 1 is a mixture of hexapeptides. Theoretically, all possible peptides containing 17 different amino acids (see below) are included. The mixture does not contain any lysine and cysteine residue. Furthermore, the mixture does not contain:

aspartic acid at the specific position 1,
alanine at the specific position 2,
glutamic acid at the specific position 3,
phenylalanine at the specific position 4,
arginine at the specific position 5, and
histidine at the specific position 6.

The synthesis is performed on an Applied Biosystems 431A-Synthesizer following the FastMoc protocol, with a synthesis scale of 0.25 mmol.

The synthesis starts with weighing 1 mmol of all desired amino acids (amino groups and side chains protected). Then, a mixture of Asn, Gln, Gly, Ile, Leu, Met, Pro, Ser, Thr, Trp, Tyr, Val was produced. Position-specific, the following amino acids are added:

Ala, Glu, Phe, Arg, His (position/mixture 1),
Asp, Glu, Phe, Arg, His (position/mixture 2),
Asp, Ala, Phe, Arg, His (position/mixture 3),
Asp, Ala, Glu, Arg, His (position/mixture 4),
Asp, Ala, Glu, Phe, His (position/mixture 5), and
Asp, Ala, Glu, Phe, Arg (position/mixture 6, without Pro).

Mixture 6 was used to load the resin (2-chloro-tritylchloride resin, 1.49 mmol/g, Alexis Germany):

1 mmol amino acid residue mixture 6
611 mg resin (=0.91 mmol reactive groups)
15 ml dichloromethane
5.5 equivalent=5 mmol diisopropylethylamine (871 µl).

The mixture is shaken in a flask for 1 h. Then, 1 ml methanol is added and the mixture is shaken for an additional 10 min. The loaded resin is extracted via a frit and washed twice with dimethylformamide, dichlormethane, isopropanol, methanol, and ether (30 ml of each). The drying is performed overnight in a high vacuum. The weigh-out quantity is 737 mg.

An aliquot of 5.66 mg is treated for 30 min with 1 ml of 20% piperidine in DMF to define the density of the resin. Then, the mixture is centrifuged. The free Fmoc protective group is photometrically measured in the supernatant (301 nm, coefficient of extinction=7800 M (e−1)). Accordingly, the density of the resin is 0.49 mmol/g.

All following steps are performed at the synthesizer, using the other mixtures (put in 5 different cartridges). 515 mg of loaded resin are used (corresponding to 0.25 mmol: amino acid mixtures are used in 4-times excess). The N-terminal Fmoc protective group is cleaved at the end of the synthesis. After washing with ethanol and drying overnight, cleavage of the peptides from the resin is accomplished by TFA/H$_2$O (95:5, v:v). The TFA solution is concentrated in a Speed Vac to ⅕ volume and precipitated and washed in diethylether and lyophilized.

The 6mer peptides EIDYHR (SEQ ID NO: 91), ELDYHR (SEQ ID NO: 92), and EVDYHR (SEQ ID NO: 93) are examples for mimotopes that can be detected by the monoclonal antibody produced according to example 1 above.

2.2.: Library 2: This 6-mer library contains peptides with the following sequences (amino acid positions 1 to 6):

Position 1: D (fixed)
Position 2: all natural as except of A, K, and C (17 possibilities)
Position 3: all natural as except of E, K, and C (17 possibilities)
Position 4: all natural as except of F, K, and C (17 possibilities)
Position 5: all natural as except of R, K, and C (17 possibilities)
Position 6: all natural as except of H, K, C, and P (16 possibilities).

Peptide library 2 was constructed according to the method described above (under 2.1) for library 1.

The 6mer peptides DIDYHR (SEQ ID NO: 94), DLDYHR (SEQ ID NO: 95), and DVDYHR (SEQ ID NO: 96) are examples for mimotopes that can be detected by the monoclonal antibody produced according to 1 above.

2.3.: Library 3: A third peptide library is used in an addition-al approach to define mimotope sequences. This library contains the original sequence, and allows the detection of mimotopes more closely related to the original epitope.

This 6-mer library contains peptides with the following sequences (amino acid positions 1 to 6):

Position 1: all natural as except of K, and C (18 possibilities)
Position 2: all natural as except of K, and C (18 possibilities)
Position 3: all natural as except of K, and C (18 possibilities)
Position 4: all natural as except of K, and C (18 possibilities)
Position 5: all natural as except of K, and C (18 possibilities)
Position 6: all natural as except of K, C, and P (17 possibilities).

Peptide library 3 was constructed according to the method described above (under 2.1) for library 1.

The 6mer peptides DLDYRR (SEQ ID NO: 97), DLDYRR (SEQ ID NO: 98), and DVDYRR (SEQ ID NO: 99) are examples for mimotopes that can be detected by the monoclonal antibody produced according to 1. above (D in position 1 and R in position 5 are identical with the original epitope).

2.4.: Library 4: This peptide library 4 consists of 5×18=90 peptides, is commercially available from Mimotopes Ltd. (Paris, France; see manufacturer's guidelines) and is designed according to the natural N-terminal Aβ/42 sequence DAEFRH (SEQ ID NO: 1).

Position 1: D (fixed)
Position 2: all natural amino acids except of K and C (18 different peptides)
Position 3: all natural amino acids except of K and C (18 different peptides)
Position 4: all natural amino acids except of K and C (18 different peptides)
Position 5: all natural amino acids except of K and C (18 different peptides)
Position 6: all natural amino acids except of K and C (18 different peptides).

The individualised peptide members of library 4 are depicted in FIG. 1. Peptides no. 1, 24, 48, 56 and 80 have the original sequence of the Aβ42 N-terminal sequence. All other peptides are candidate peptides which are tested with respect to their binding capacity to a DAEFRH-binding antibody (DAEFRH sequence disclosed as SEQ ID NO: 1).

2.5.: ELISA with peptide libraries:

As mentioned above, peptide libraries 1, 2, and 3 are generated with an Applied Biosystems 431A peptide synthesizer following classical Fmoc-chemistry. The commercially available peptide library 4 is generated according to the manufacturer's description (see above and under www-.mimotopes.com). The 90 peptides are C-terminally linked to a pin.

The ELISA with each of the peptide libraries have been carried out following standard protocols:

The peptide library is dissolved in 100% DMSO (final concentration 10 mg/ml).

The peptide solution is further diluted in PBS.

The peptide mixture is coated overnight (4° C.) onto ELISA plates (Nunc Maxisorp, Germany), starting with 500 µg/well, and titrated to 100 ng/well.

The plates are washed 3× times with PBS/Tween 20 (0.1% v/v).

The plates are blocked with PBS/BSA (2 h at room temperature).

The plates are washed 3× times with PBS/Tween.

The plates are incubated with biotinylated DAEFRH-specific mAb (DAEFRH sequence disclosed as SEQ ID NO: 1) (10 µg/ml in PBS) for 4 h at room temperature.

The plates are washed 3× times with PBS/Tween.

The plates are incubated with streptavidin-horseradish-peroxidase (30 min at room temperature).

The plates are washed 5× times with PBS/Tween.

The plates are incubated with ABTS+H2O2 (0.1% w/v; 10 to 45 min) and the reaction is stopped with citric acid followed by photometric evaluation (wavelength 405 nm).

3.: Verification of Mimotopes by Inhibition Assay 3.1. Additional Library

In addition to the 4 libraries described above (see 2.1., 2.2., 2.3., and 2.4.) a fifth library is used to define mimotope sequences. This 6mer library is commercially available at EMC microcollections (Tubingen Germany) and contains 114 different hexapeptide mixtures, one position per mixture is defined by one of all natural as except of C (19 possibilities), the remaining 5 positions are variable:

Mixtures 01 to 06 (one position fixed, alanine A, remaining 5 variable, X):
Mixture 01: AXXXXX
Mixture O₂: XAXXXX
Mixture 03: XXAXXX
Mixture 04: XXXAXX
Mixture 05: XXXXAX
Mixture 06: XXXXXA Mixtures 07- to 12 (one position fixed, arginine R, remaining 5 variable, X):
Mixture 07: RXXXXX
Mixture 08: XRXXXX
Mixture 09: XAXXXX
Mixture 10: XXAXXX
Mixture 11: XXXXRX
Mixture 12: XXXXXR Accordingly, mixtures 13 to 114 are designed using all natural as except of C.

3.2. Inhibition Assay

FIGS. 2 and 3 describe the results of inhibition assays performed with mimotope peptides included in and obtained from the 5 libraries (as described). The mimotope peptides compete with the original epitope for recognition by the monoclonal antibody. Original epitope and mimotope peptides contain an additional C at the C-terminus for coupling to a protein carrier (if desired).

The following peptides are used:
Peptide 1737 DAEFRH (SEQ ID NO: 1)
Peptide 3001 DKELRI (SEQ ID NO: 100)
Peptide 3002 DWELRI (SEQ ID NO: 101)
Peptide 3003 YREFFI (SEQ ID NO: 119)
Peptide 3004 YREFRI (SEQ ID NO: 102)
Peptide 3005 YAEFRG (SEQ ID NO: 103)
Peptide 3006 EAEFRG (SEQ ID NO: 104)
Peptide 3007 DYEFRG (SEQ ID NO: 105)
Peptide 3008 ELEFRG (SEQ ID NO: 106)
Peptide 3009 SFEFRG (SEQ ID NO: 115)
Peptide 3010 DISFRG (SEQ ID NO: 120)
Peptide 3011 DIGWRG (SEQ ID NO: 121)

Procedure:

ELISA plates (Nunc Maxisorp) are coated with the original peptide epitope DAEFRH (SEQ ID NO: 1) (C-terminally prolonged with C and coupled to bovine serum albumin BSA) at a concentration of 0.1 µg/ml peptide-BSA (100 µl/well, 12 h, 4° C.). After blocking with PBS/BSA 1% (200 µl/well, 12 h, 4° C.), the plates are washed 3× times with PBS/Tween. Then, biotinylated monoclonal antibody (1:2000, 50 µl/well) and peptides (50 µl/well) at 50, 5, 0.5, 0.05, 0.005, and 0.0005 µg/ml are added for 20 min. at 37° C. The plates are washed 3× times with PBS/Tween and are incubated with horseradish peroxidase (HRP)-labeled streptavidin (100 µl/well, 30 min, RT). The plates are washed 5× times with PBS/Tween and are incubated with ABTS+H2O2 (0.1% w/v, 10 to 45 min) and the reaction is stopped with citric acid followed by photometric evaluation (wavelength 405 nm).

As expected and seen in FIG. 2, peptide 1737 DAEFRH (SEQ ID NO: 1) can compete with BSA-coupled, plate-bound peptide DAEFRH (SEQ ID NO: 1) and thus inhibits recognition by the monoclonal antibody. Furthermore, it is shown that peptide 3003 is not able to inhibit binding of the monoclonal antibody to the original epitope. In contrast, peptides 3001, 3002, 3004, 3005, 3006, and 3007 (to a different extent) block epitope recognition. Whereas peptide 3004 is only inhibitory at a high concentration (50 µg/ml), peptides 3001, 3006, and 3007 are strongly inhibitory with an IC50 of less than 0.5 µg/ml. Peptides 3002 and 3005 are "intermediate" inhibitors with an IC50 of more than 0.5 µg/ml.

As expected and seen in FIG. 3, peptide 1737 DAEFRH (SEQ ID NO: 1) can successfully compete with BSA-coupled, plate-bound peptide DAEFRH (SEQ ID NO: 1) for monoclonal antibody recognition in an additionally performed, independent experiment. Furthermore, it is shown that peptides 3010 and 3011 are not inhibitory at the concentrations tested, whereas peptides 3008 and 3009 are (relatively) weak inhibitors with an IC50 of less than 5 µg/ml.

Table 1 briefly summarizes the inhibitory capacity of mimotopes included in and obtained from libraries (as described):

Table 1: Inhibitory capacity of mimotopes:
Peptide 3001 DWELRI (SEQ ID NO: 100) strong
Peptide 3002 DWELRI (SEQ ID NO: 101) intermediate
Peptide 3003 YREFFI (SEQ ID NO: 119) none
Peptide 3004 YREFRI (SEQ ID NO: 102) weak
Peptide 3005 YAEFRG (SEQ ID NO: 103) intermediate
Peptide 3006 EAEFRG (SEQ ID NO: 104) strong
Peptide 3007 DYEFRG (SEQ ID NO: 105) strong
Peptide 3008 ELEFRG (SEQ ID NO: 106) weak
Peptide 3009 SFEFRG (SEQ ID NO: 115) weak
Peptide 3010 DISFRG (SEQ ID NO: 120) none
Peptide 3011 DIGWRG (SEQ ID NO: 121) none

4. Inhibition Assay for Additional Mimotopes Screenend According to the Present Invention Inhibition Assay FIGS. 4 and 5 describe the results of inhibition assays performed with mimotope peptides included in and obtained from the 5 libraries (as described). The mimotope peptides compete with the original epitope for recognition by the monoclonal antibody. Original epitope and mimotope peptides contain an additional C at the C-terminus (position 7) for coupling to a protein carrier (if desired).

The following peptides are used:
Peptide 1737 DAEFRH (SEQ ID NO: 1) (original epitope+ C)
  Peptide 1234 KKELRI (SEQ ID NO: 122)
  Peptide 1235 DRELRI (SEQ ID NO: 107)
  Peptide 1236 DKELKI (SEQ ID NO: 108)
  Peptide 1237 DRELKI (SEQ ID NO: 109)
  Peptide 1238 DKELR (SEQ ID NO: 114)
  Peptide 1239 EYEFRG (SEQ ID NO: 111)
  Peptide 1241 DWEFRDA (SEQ ID NO: 112)
  Peptide 4002 SWEFRT (SEQ ID NO: 113)
  Peptide 4003 GREFRN (SEQ ID NO: 110)
  Peptide 4004 WHWSWR (SEQ ID NO: 123)

Procedure:

ELISA plates (Nunc Maxisorp) are coated with the original peptide epitope DAEFRH (SEQ ID NO: 1) (C-terminally prolonged with C and coupled to bovine serum albumin BSA) at a concentration of 0.1 µg/ml peptide-BSA (100 µl/well, 12 h, 4° C.). After blocking with PBS/BSA 1% (200 µl/well, 12 h, 4° C.), the plates are washed 3× times with PBS/Tween. Then, biotinylated monoclonal antibody (1:2000, 50 µl/well) and peptides (50 µl/well) at different concentrations are added for 20 min. at 37° C. The plates are washed 3× times with PBS/Tween and are incubated with horseradish peroxidase (HRP)-labeled streptavidin (100 µl/well, 30 min, RT). The plates are washed 5× times with PBS/Tween and are incubated with ABTS H2O2 (0.1% w/v, 10 to 45 min) and the reaction is stopped with citric acid followed by photometric evaluation (wavelength 405 nm).

Figure 4:
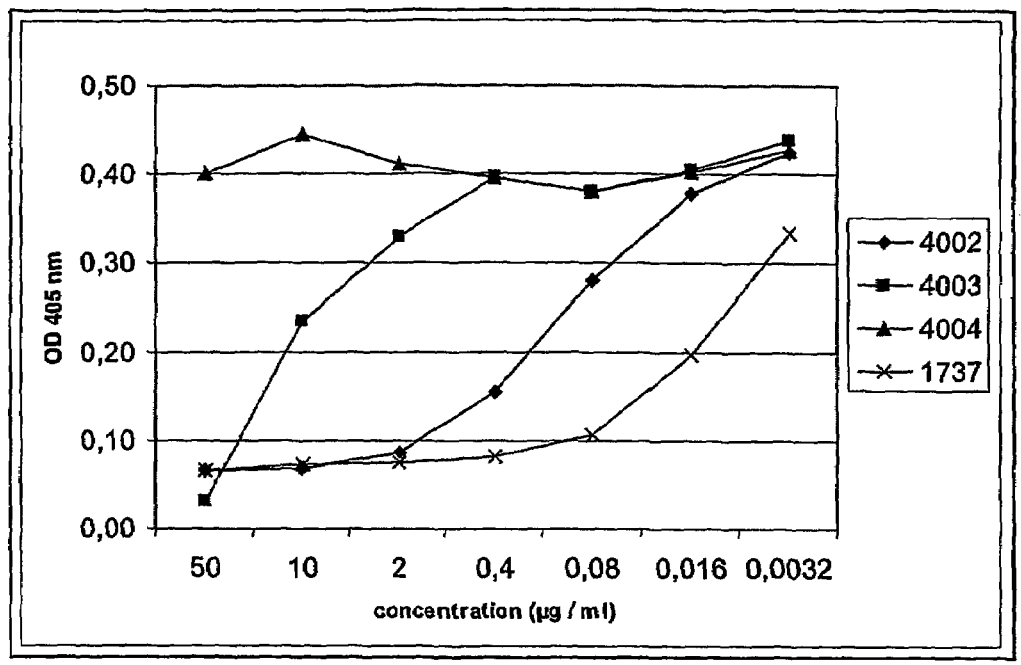
FIGS. 4 and 5 describe the results of inhibition assays performed with mimotope peptides according to the present invention.

As expected and seen in FIG. 4, peptide 1737 DAEFRH (SEQ ID NO: 1) can compete with BSA-coupled, plate-bound peptide DAEFRH (SEQ ID NO: 1) and thus inhibits recognition by the monoclonal antibody. Furthermore, it is shown that peptide 4004 is not able to inhibit binding of the monoclonal antibody to the original epitope. In contrast, peptides 4002 and 4003 (to a different extent) block epitope recognition. Whereas peptide 4003 is only inhibitory at a relatively high concentration (10 µg/ml), peptide 4002 is strongly inhibitory with an IC50 of less than 0.4 µg/ml.

Figure 5:
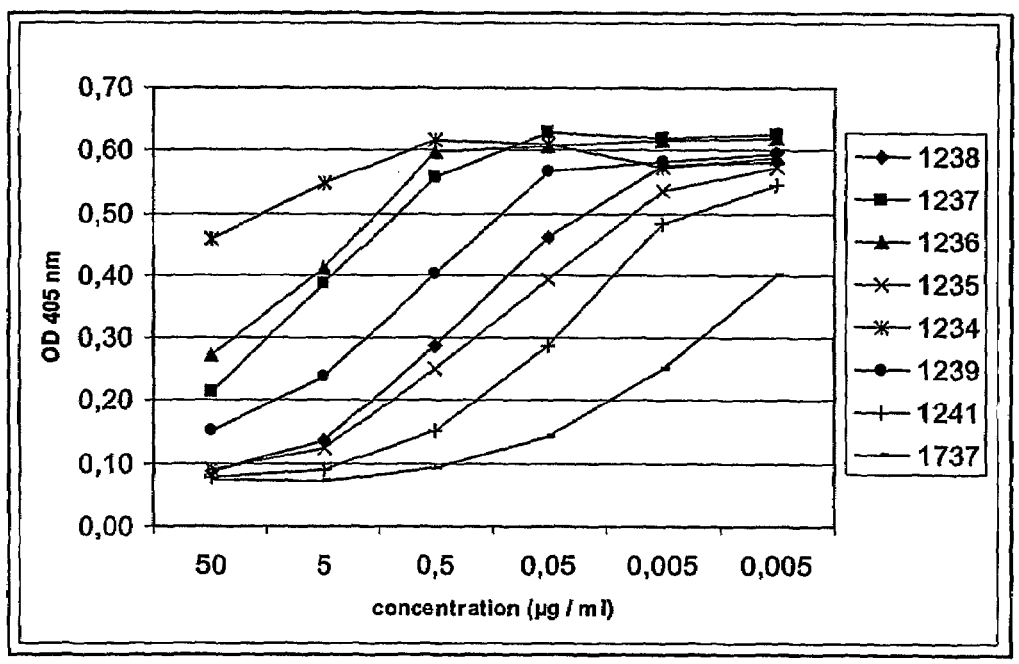

As expected and seen in FIG. 5, peptide 1737 DAEFRH (SEQ ID NO: 1) can successfully compete with BSA-coupled, plate-bound peptide DAEFRH (SEQ ID NO: 1) for monoclonal antibody recognition in an additionally performed, independent experiment. Furthermore, it is shown that peptide 1234 is hardly inhibitory at the concentrations tested, whereas peptides 1235, 1236, 1237, 1238, 1239 and 1241 (to a different extent) block epitope recognition. Peptides 1235, 1238 and 1241 are strong inhibitors with an IC50 of less than 0.5 µg/ml, whereas peptides 1236 and 1237 are (relatively) weak inhibitors with an IC50 of more than 5 µg/ml. Peptide 1239 is an intermediate inhibitor with an IC50 of more than 0.5 µg/ml.

Table 2 briefly summarizes the inhibitory capacity of mimotopes included in and obtained from libraries (as described):

Table 2: Inhibitory capacity of mimotopes:
  Peptide 1234 KKELRI (SEQ ID NO: 122) none
  Peptide 1235 DRELRI (SEQ ID NO: 107) strong
  Peptide 1236 DKELKI (SEQ ID NO: 108) weak
  Peptide 1237 DRELKI (SEQ ID NO: 109) weak
  Peptide 1238 DKELR (SEQ ID NO: 114) strong
  Peptide 1239 EYEFRG (SEQ ID NO: 111) intermediate
  Peptide 1241 DWEFRDA (SEQ ID NO: 112) strong
  Peptide 4002 SWEFRT (SEQ ID NO: 113) strong
  Peptide 4003 GREFRN (SEQ ID NO: 110) weak
  Peptide 4004 WHWSWR (SEQ ID NO: 123) none The results presented in FIGS. 4 and 5 show that in addition to various 6mer peptides (as shown here and before), 5mer peptides (namely peptide 1238 DKELR (SEQ ID NO: 114)) and 7mer peptides (namely peptide 1241 DWEFRDA (SEQ ID NO: 112)) may be used as epitopes in a mimotope-based Alzheimer vaccine.

The invention claimed is:

1. An isolated and purified compound, which comprises a sequence selected from the group consisting of EIDYHR (SEQ ID NO: 91), ELDYHR (SEQ ID NO: 92), EVDYHR (SEQ ID NO: 93), DIDYHR (SEQ ID NO: 94), DLDYHR (SEQ ID NO: 95), DVDYHR (SEQ ID NO: 96), DIDYRR (SEQ ID NO: 97), DLDYRR (SEQ ID NO: 98), DVDYRR (SEQ ID NO: 99), DKELRI (SEQ ID NO: 100), DWELRI (SEQ ID NO: 101), YREFFI (SEQ ID NO: 119), YREFRI (SEQ ID NO: 102), YAEFRG (SEQ ID NO: 103), EAEFRG (SEQ ID NO: 104), DYEFRG (SEQ ID NO: 105), ELEFRG (SEQ ID NO: 106), DRELRI (SEQ ID NO: 107), DKELKI (SEQ ID NO: 108), DRELKI (SEQ ID NO: 109), GREFRN (SEQ ID NO: 110), EYEFRG (SEQ ID NO: 111), DWEFRDA (SEQ ID NO: 112), SWEFRT (SEQ ID NO: 113), and SFEFRG (SEQ ID NO: 115), wherein said compound binds to an antibody specific for DAEFRH (SEQ ID NO: 1) and wherein the compound consists of not more than 15 amino acid residues.

2. The compound of claim 1, further comprising covalently-coupled carrier.

3. The compound of claim 2, wherein said carrier is a peptide linker or a polypeptide.

4. The compound of claim 2, wherein said carrier is selected from the group consisting of KLH, tetanus toxoid, albumin binding protein, bovine serum albumin and dendrimer.

5. A composition comprising the compound of claim 1 and a pharmaceutically acceptable carrier or adjuvant.

6. The composition of claim 5, which comprises a non-covalently associated peptide linker or protein carrier.

7. The composition of claim 5, which comprises aluminum hydroxide.

8. The composition of claim 5 which comprises 0.1 ng to 10 mg of said compound.

9. The composition of claim 5, which comprises 100 ng to 100 µg of said compound.

10. The compound of claim 1, which comprises EIDYHR (SEQ ID NO: 91).

11. The compound of claim 1, which comprises ELDYHR (SEQ ID NO: 92).

12. The compound of claim 1, which comprises EVDYHR (SEQ ID NO: 93).

13. The compound of claim 1, which comprises DIDYHR (SEQ ID NO: 94).

14. The compound of claim 1, which comprises DLDYHR (SEQ ID NO: 95).

15. The compound of claim 1, which comprises DVDYHR (SEQ ID NO: 96).

16. The compound of claim 1, which comprises DIDYRR (SEQ ID NO: 97).

17. The compound of claim 1, which comprises DLDYRR (SEQ ID NO: 98).

18. The compound of claim 1, which comprises DVDYRR (SEQ ID NO: 99).

19. The compound of claim 1, which comprises DKELRI (SEQ ID NO: 100).

20. The compound of claim 1, which comprises DWELRI (SEQ ID NO: 101).

21. The compound of claim 1, which comprises YREFFI (SEQ ID NO: 119).

22. The compound of claim 1, which comprises YREFRI (SEQ ID NO: 102).

23. The compound of claim 1, which comprises YAEFRG (SEQ ID NO: 103).

24. The compound of claim 1, which comprises EAEFRG (SEQ ID NO: 104).

25. The compound of claim 1, which comprises DYEFRG (SEQ ID NO: 105).

26. The compound of claim 1, which comprises ELEFRG (SEQ ID NO: 106).

27. The compound of claim 1, which comprises DRELRI (SEQ ID NO: 107).

28. The compound of claim 1, which comprises DKELKI (SEQ ID NO: 108).

29. The compound of claim 1, which comprises DRELKI (SEQ ID NO: 109).

30. The compound of claim 1, which comprises GREFRN (SEQ ID NO: 110).

31. The compound of claim 1, which comprises EYEFRG (SEQ ID NO: 111).

32. The compound of claim 1, which comprises DWEFRDA (SEQ ID NO: 112).

33. The compound of claim 1, which comprises SWEFRT (SEQ ID NO: 113).

34. The compound of claim 1, which comprises SFEFRG (SEQ ID NO: 115).

* * * * *

SEQUENCE LISTING

```
<160> NUMBER OF SEQ ID NOS: 123

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Ala Glu Phe Arg His
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
                               peptide

<400> SEQUENCE: 2

Asp Arg Glu Phe Arg His
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Asn Glu Phe Arg His
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Asp Glu Phe Arg His
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Gln Glu Phe Arg His
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Glu Glu Phe Arg His
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Gly Glu Phe Arg His
1               5

<210> SEQ ID NO 8
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp His Glu Phe Arg His
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Ile Glu Phe Arg His
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Leu Glu Phe Arg His
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Met Glu Phe Arg His
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Phe Glu Phe Arg His
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13
```

```
Asp Pro Glu Phe Arg His
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Ser Glu Phe Arg His
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Thr Glu Phe Arg His
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Trp Glu Phe Arg His
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Tyr Glu Phe Arg His
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Val Glu Phe Arg His
1               5

<210> SEQ ID NO 19
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 19

Asp Ala Ala Phe Arg His
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Ala Arg Phe Arg His
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Ala Asn Phe Arg His
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Ala Asp Phe Arg His
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Ala Gln Phe Arg His
1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Ala Glu Phe Arg His
1               5
```

```
<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Ala Gly Phe Arg His
1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Ala His Phe Arg His
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Ala Ile Phe Arg His
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Ala Leu Phe Arg His
1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Ala Met Phe Arg His
1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30
```

Asp Ala Phe Phe Arg His
1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Ala Pro Phe Arg His
1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asp Ala Ser Phe Arg His
1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asp Ala Thr Phe Arg His
1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Ala Trp Phe Arg His
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asp Ala Tyr Phe Arg His
1               5

<210> SEQ ID NO 36
<211> LENGTH: 6
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 36

Asp Ala Val Phe Arg His
1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Ala Glu Ala Arg His
1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Ala Glu Arg Arg His
1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Ala Glu Asn Arg His
1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Ala Glu Asp Arg His
1               5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asp Ala Glu Gln Arg His
1               5
```

```
<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Ala Glu Glu Arg His
1               5

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asp Ala Glu Gly Arg His
1               5

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Ala Glu His Arg His
1               5

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Ala Glu Ile Arg His
1               5

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Ala Glu Leu Arg His
1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 47

Asp Ala Glu Met Arg His
1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asp Ala Glu Phe Arg His
1               5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asp Ala Glu Pro Arg His
1               5

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asp Ala Glu Ser Arg His
1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Ala Glu Thr Arg His
1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Ala Glu Trp Arg His
1               5

<210> SEQ ID NO 53
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 53

Asp Ala Glu Tyr Arg His
1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Ala Glu Val Arg His
1               5

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asp Ala Glu Phe Ala His
1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asp Ala Glu Phe Arg His
1               5

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asp Ala Glu Phe Asn His
1               5

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Ala Glu Phe Asp His
1               5
```

-continued

```
<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asp Ala Glu Phe Gln His
1               5

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asp Ala Glu Phe Glu His
1               5

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asp Ala Glu Phe Gly His
1               5

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asp Ala Glu Phe His His
1               5

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asp Ala Glu Phe Ile His
1               5

<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 64

Asp Ala Glu Phe Leu His
1               5

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Asp Ala Glu Phe Met His
1               5

<210> SEQ ID NO 66
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asp Ala Glu Phe Phe His
1               5

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Asp Ala Glu Phe Pro His
1               5

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Ala Glu Phe Ser His
1               5

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Ala Glu Phe Thr His
1               5

<210> SEQ ID NO 70
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asp Ala Glu Phe Trp His
1               5

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp Ala Glu Phe Tyr His
1               5

<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asp Ala Glu Phe Val His
1               5

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asp Ala Glu Phe Arg Ala
1               5

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Asp Ala Glu Phe Arg Arg
1               5

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Asp Ala Glu Phe Arg Asn
```

-continued

```
1               5

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Asp Ala Glu Phe Arg Asp
1               5

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Asp Ala Glu Phe Arg Gln
1               5

<210> SEQ ID NO 78
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp Ala Glu Phe Arg Glu
1               5

<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Asp Ala Glu Phe Arg Gly
1               5

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asp Ala Glu Phe Arg His
1               5

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
                                     peptide

<400> SEQUENCE: 81

Asp Ala Glu Phe Arg Ile
1               5

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asp Ala Glu Phe Arg Leu
1               5

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asp Ala Glu Phe Arg Met
1               5

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Asp Ala Glu Phe Arg Phe
1               5

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Asp Ala Glu Phe Arg Pro
1               5

<210> SEQ ID NO 86
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Asp Ala Glu Phe Arg Ser
1               5

<210> SEQ ID NO 87
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Asp Ala Glu Phe Arg Thr
1               5

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asp Ala Glu Phe Arg Trp
1               5

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Asp Ala Glu Phe Arg Tyr
1               5

<210> SEQ ID NO 90
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Asp Ala Glu Phe Arg Val
1               5

<210> SEQ ID NO 91
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Glu Ile Asp Tyr His Arg
1               5

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92
```

-continued

Glu Leu Asp Tyr His Arg
1               5

<210> SEQ ID NO 93
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Glu Val Asp Tyr His Arg
1               5

<210> SEQ ID NO 94
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Asp Ile Asp Tyr His Arg
1               5

<210> SEQ ID NO 95
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Asp Leu Asp Tyr His Arg
1               5

<210> SEQ ID NO 96
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Asp Val Asp Tyr His Arg
1               5

<210> SEQ ID NO 97
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Asp Ile Asp Tyr Arg Arg
1               5

<210> SEQ ID NO 98
<211> LENGTH: 6
<212> TYPE: PRT
<213> ORGANISM: Artificial Sequence
<220> FEATURE:

-continued

<223> OTHER INFORMATION: Description of Artificial Sequence: Synthetic
      peptide

<400> SEQUENCE: 98

Asp Leu Asp Tyr Arg Arg
1               5

<210> SEQ ID NO 99
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Asp Val Asp Tyr Arg Arg
1               5

<210> SEQ ID NO 100
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Asp Lys Glu Leu Arg Ile
1               5

<210> SEQ ID NO 101
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Asp Trp Glu Leu Arg Ile
1               5

<210> SEQ ID NO 102
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Tyr Arg Glu Phe Arg Ile
1               5

<210> SEQ ID NO 103
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Tyr Ala Glu Phe Arg Gly
1               5

```
<210> SEQ ID NO 104
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Glu Ala Glu Phe Arg Gly
1               5

<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Asp Tyr Glu Phe Arg Gly
1               5

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Glu Leu Glu Phe Arg Gly
1               5

<210> SEQ ID NO 107
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Asp Arg Glu Leu Arg Ile
1               5

<210> SEQ ID NO 108
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asp Lys Glu Leu Lys Ile
1               5

<210> SEQ ID NO 109
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109
```

```
Asp Arg Glu Leu Lys Ile
1               5

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Arg Glu Phe Arg Asn
1               5

<210> SEQ ID NO 111
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Glu Tyr Glu Phe Arg Gly
1               5

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Asp Trp Glu Phe Arg Asp Ala
1               5

<210> SEQ ID NO 113
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ser Trp Glu Phe Arg Thr
1               5

<210> SEQ ID NO 114
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Asp Lys Glu Leu Arg
1               5

<210> SEQ ID NO 115
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 115

Ser Phe Glu Phe Arg Gly
1               5

<210> SEQ ID NO 116
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ser Glu Val Lys Met Asp Ala Glu Phe Arg His
1               5                   10

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Met Asp Ala Glu Phe Arg His
1               5

<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Lys Met Asp Ala Glu Phe Arg His
1               5

<210> SEQ ID NO 119
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Tyr Arg Glu Phe Phe Ile
1               5

<210> SEQ ID NO 120
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Asp Ile Ser Phe Arg Gly
1               5
```

```
<210> SEQ ID NO 121
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Asp Ile Gly Trp Arg Gly
1               5

<210> SEQ ID NO 122
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Lys Lys Glu Leu Arg Ile
1               5

<210> SEQ ID NO 123
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Trp His Trp Ser Trp Arg
1               5
```